United States Patent [19]

Close

[11] Patent Number: 4,665,030

[45] Date of Patent: May 12, 1987

[54] PROCESS FOR REGENERATING CORN

[75] Inventor: Kelly R. Close, Palo Alto, Calif.

[73] Assignee: Sungene Technologies Corporation, Palo Alto, Calif.

[21] Appl. No.: 648,389

[22] Filed: Sep. 7, 1984

[51] Int. Cl.$^4$ .......................... C12N 5/00; C12N 5/02
[52] U.S. Cl. ..................................... 435/240; 435/241
[58] Field of Search ................................. 435/240, 241

[56] References Cited

PUBLICATIONS

Vasil (Editor) 1984, *Cell Culture and Somatic Cell Genetics of Plants*, Academic Press, pp. 19–21 and 26.
Conger (Editor) 1981, *Cloning Agricultural Plants Via in Vitro Techniques*, CRC Press, pp. 13, 175.
Dudits et al, 1975, "Study of Callus Growth and Organ Formation in Wheat (Triticum Aestivum)", *Can J. Bot.*, vol. 53, pp. 957–963.
Earle et al, 1982, *Variability in Plants Regenerated from Tissue Culture*, Praeger, p. 6.
Evans et al, 1983, *Handbook of Plant Cell Culture*, vol. 1, Macmillan Publ. Co., pp. 101–102.
Green, C. E., et al., *Crop Science* 15, 417 (1975).
Freeling, M., et al., *Maydica* 21, 97 (1976).
Lu, C., et al., *Theor. Appl. Genet.* 66, 285 (1983).
Edallo, S., et al., *Maydica* 26, 39 (1981).
Lu, C., et al., *Theor. Appl. Genet.* 62, 109 (1982).
Hibberd, K. A., et al., *Proc. Natl. Acad. Sci. USA* 79, 559 (1982).
Gengenbach, B. G. et al., *Proc. Natl. Acad. Sci. USA* 74, 5113 (1977).
Green, C. E., et al., *Crop Science* 14, 54 (1974).
Irvine, J. E., et al., *Plant Cell Tissue Organ Culture* 2, 141 (1983).
Hanning, G. E., et al., *Theor. Appl. Genet.* 63, 155 (1982).
Conger, B. V., et al., *Science* 221, 850 (1983).

*Primary Examiner*—Thomas G. Wiseman
*Assistant Examiner*—David T. Fox
*Attorney, Agent, or Firm*—Robbins & Laramie

[57] ABSTRACT

The present invention relates to the regeneration of corn. The process comprises the steps of:

(a) culturing tissue obtained from a corn plant on a first medium which comprises mineral salts, vitamins sucrose and a hormone in an amount sufficient to ensure callus formation;

(b) subculturing the calli on a second medium which comprises mineral salts, vitamins, sucrose and a hormone in an amount sufficient to ensure callus maintenance;

(c) subculturing the calli on a third medium which comprises mineral salts, vitamins, sucrose and a hormone in an amount sufficient to ensure shoot and root formation; and (d) optionally subculturing said shoots on a fourth medium which comprises mineral salts, vitamins, sucrose and a hormone in an amount sufficent to ensure plantlet maturation including additional root formation, whereby plants are obtained.

19 Claims, No Drawings

PROCESS FOR REGENERATING CORN

BACKGROUND OF THE INVENTION

1. Field of the Invention

The present invention relates to a general process for regenerating corn and to plants produced by the process. More particularly, the present invention relates to the use of tissue and cell culture for the regeneration of corn plantlets from many varieties of corn.

2. Description of the Prior Art

Plant regeneration from cells in culture is essential for the application of somatic hybridization, for the production of new varieties through somoclonal variation and for the use of genetic engineering in producing new varieties. Although plants can be regenerated from tissue culture of several varieties of corn, there are many varieties for which this has not been accomplished using similar techniques.

In recent years, plant cell culture successes have had a considerable influence on the respective roles of cell and organism in control of plant growth and development. This concept was supported when isolated plant cells were shown to be amenable to in vitro cultivation and complete plants could be regenerated from cultures derived from somatic tissues, either directly via somatic embryogenesis or indirectly via organogenesis. Generally the regeneration pathway of choice is determined empirically by the manipulation of extrinsic factors, especially growth regulators. Early investigations of certain plant species have suggested that exogenous auxin concentration is a major factor controlling somatic embryogenesis, such that its reduction leads to the initiation of embryoid formation. In other species, exposure to a definite balance of auxin and cytokinin leads to the occurrance of organogenesis (shoots, then roots). Although several genotypes of corn have been regenerated using these techniques, no process is generally applicable to most genotypes of corn. Many genotypes remain extremely difficult if not impossible to culture using the prior processes.

The process which has become the standard system for corn tissue culture is described by Green et al., *Crop Science* 15, 417 (1975). In this process, immature embryos were plated onto a callus induction medium which comprises the MS mineral salts, Straus vitamins and amino acids (glycine, asparagine, niacin, thiamine, pyridoxine and pantothenic acid), 2% sucrose, 0.8% agar and a hormone selected from 2,4-dichlorophenoxyacetic acid (2,4-D), p-chlorophenoxyacetic acid (PCA), alpha-naphthaleneacetic acid (NAA), 2-isopentyladedine (2-ip) or mixtures thereof. Plantlets were regenerated by subculturing the callus on medium containing reduced hormone concentrations. Hormone concentrations which were useful were 2 mg/l 2,4-D and a mixture of 1 mg/l 2,4-D, 4 mg/l NAA and 0.05 mg/l 2-ip. Regeneration was then accomplished on medium containing 0.25 mg/l 2,4-D or a mixture of 1 mg/l NAA and 0.05 mg/l 2-ip respectively. All culturing was conducted in a 16 hour light/8 hour dark cycle for 3-4 week intervals before transfer. This reference reports that callus induction did not occur in one of five genotypes tested.

Similar results have been reported by others. Freeling et al., *Maydica* 21, 97 (1976) obtained regeneration of corn by utilizing a sequence of callus induction on a RM medium containing 2 or 5 mg/l 2,4-D, 2% sucrose and no myo-inositol followed by regeneration on the same medium with 0-0.1 mg/l 2,4-D. Lu et al., *Theor. Appl. Genet.* 66, 285 (1983) obtained callus formation and shoot formation after 3 weeks of culturing when utilizing a MS medium containing 3-12% sucrose and 0.25-2.0 mg/l 2,4-D. High sucrose concentration was most favorable for embryogenic callus. Root formation was accomplished after transfer to (a) MS medium with 3% sucrose with or without 1 mg/l giberellic acid ($GA_3$) or (b) ½ MS medium with 2% sucrose.

Edallo et al., *Maydica* 26, 39 (1981) obtained callus induction from immature corn embryos using the medium of Green et al., supra, with 2 mg/l 2,4-D. The culture could be maintained on the same medium with 30 day transfers. Regeneration was accomplished by using medium with no 2,4-D. Shoots were transferred to medium having a 1 mm overlayer of 5 mg/l NAA for root formation. Prior to transferring the plantlets to soil, they were cycled through media having 20%, 10% and finally 0% sucrose. Regeneration of corn plants using a similar sequence of callus induction with 2,4-D and regeneration with no or low 2,4-D has been shown by Lu et al., *Theor. Appl. Genet.* 62, 109 (1982); Hibberd et al., *Proc. Natl. Acad. Sci. USA* 79, 559 (1982); Gegenbach et al., *Proc. Natl. Acad. Sci. USA* 74, 5113 (1977); and Green at al., *Crop Science* 14, 54 (1974). The latter reference also demonstrates genotype affects on callus induction.

The prior art does not describe a process for the regeneration of most genotypes of corn *Zea mays* from tissue and cell culture. Examples of cultivars that cannot be regenerated or can only be regenerated with great difficulty at low frequency by prior art processes include B73, A632, A619, CM105, B37, B84, B14, Mo17 and R168. The present invention is the first instance of a broadly and generally applicable procedure for regenerating cultivars of corn with a high frequency and with a high growth rate.

Corn plants and seeds are produced by this process. The corn plants resulting from this process may differ from the starting plant material as a result of somaclonal variation. The pathway is also useful in that it will enable the use of various selection processes to provide further variation. The plants which are produced can be used in conventional breeding programs.

SUMMARY OF THE INVENTION

The process of the present invention comprises the steps of inducing callus formation on an induction medium from tissue of a corn plant, maintaining the calli, forming shoots and roots on a regeneration medium and optionally maturing the plantlets on a maturation medium.

More specifically, the present process comprises the steps of:

(a) culturing tissue obtained from a corn plant on a first medium which comprises mineral salts, vitamins sucrose and a hormone in an amount sufficient to ensure callus formation;

(b) subculturing the calli on a second medium which comprises mineral salts, vitamins, sucrose and a hormone in an amount sufficient to ensure callus maintenance;

(c) subculturing the calli on a third medium which comprises mineral salts, vitamins, sucrose and a hormone in an amount sufficient to ensure shoot formation and root formation; and (d) optionally subculturing said shoots on a fourth medium which comprises mineral salts, vitamins, sucrose and a hormone in an amount sufficient to ensure plantlet maturation including additional root formation, whereby plants are obtained.

The source of the tissue is preferably immature embryos from cultivars of *Zea mays*. The media preferably contain N6 mineral salts and modified MS vitamins. The preferred hormones are 3,6-dichloro-2-methoxybenzoic acid (dicamba) or 3-amino-2,5-dichlorobenzoic acid (chloramben) in the first, second and third media and dicamba, chloramben or a mixture of either dicamba or chloramben and 2,4-D in the fourth medium.

DETAILED DESCRIPTION OF THE INVENTION

The present invention is directed to a process for regenerating corn, *Zea mays*, through the use of cell or tissue culture. In this process, regenerated corn plantlets are obtained which can be placed in soil and grown to maturation. The present invention is also directed to corn plants obtained by this process and seeds obtained from these plants.

In general, the process comprises (a) culturing corn plant tissue on a medium to produce calli, (b) culturing the calli on a medium to maintain the calli, (c) culturing the calli on a medium to produce shoots and roots, and (d) optionally culturing the shoots with roots on a medium to mature the plantlets for transplanting. After plantlets have been developed, they can be grown in soil.

The plant tissue which is preferred for use in the initiation of callus is the immature embryo. The immature embryos are isolated from the cob at approximately 10 days post-pollination when the embryos are 1.5-2.0 mm in length. The cob is harvested and surface sterilized. The immature embryos are isolated from each kernel. The embryos are plated onto callus induction medium, hereinafter referred to as the first medium, so that the embryo axis is in contact with the medium, i.e. the scutellar side is up.

The first medium comprises mineral salts, vitamins and sucrose. The mineral salts comprise macroelements and microelements. The macroelements used in the first medium may be the following compounds: magnesium sulfate, calcium chloride, monopotassium phosphate, potassium nitrate and ammonium sulfate. The microelements contained in the first medium are: boric acid, manganese sulfate, zinc sulfate, potassium iodide, iron (II) sulfate, disodium-ethylenediamine tetracetic acid (EDTA), sodium molybdate (VI), copper (II) sulfate and cobalt chloride. This combination of mineral salts is known in the art as the N6 mineral salts which have been modified to contain mineral salts of copper, cobalt and molybdenum. Other combinations of mineral salts may also be used as long as they do not adversely affect callus induction. Examples of combinations of mineral salts include but are not limited to MS, Heller, Nitsch and Nitsch, B5 and White.

The preferred amounts of the macroelements and microelements used to prepare one liter of the first medium are as follows: 185 mg magnesium sulfate heptahydrate, 166 mg calcium chloride dihydrate, 400 mg monopotassium phosphate, 2830 mg potassium nitrate, 463 mg ammonium sulfate, 1.6 mg boric acid, 3.3 mg manganese sulfate monohydrate, 1.5 mg zinc sulfate heptahydrate, 0.83 mg potassium iodide, 27.8 mg iron (II) sulfate heptahydrate, 37.3 mg disodium-EDTA, 0.25 mg sodium molybdate (VI) dihydrate, 0.025 mg copper (II) sulfate pentahydrate and 0.025 mg cobalt chloride hexahydrate.

The first medium also contains vitamins. The vitamins used include myo-inositol, nicotinic acid, glycine, pyridoxine, thiamine, and pantothenate. These vitamins are known in the art as the MS vitamins which have been modified to contain pantothenate.

The amounts of vitamins used to prepare one liter of the first medium are as follows: 100 mg myo-inositol, 0.5 mg nicotinic acid, 2 mg glycine, 0.5 mg pyridoxine hydrochloride and 0.1 mg thiamine hydrochloride and 0.25 mg calcium pantothenate.

The first medium contains 3-12% sucrose, preferably 9% and a gelling agent such as agar or Gelrite TM (trademark, Kelco Commercial Development). It is preferred to use Gelrite TM at a concentration of 0.18%. The medium has a pH of 5.5-6.0 with a preferred pH of 5.8.

In addition to the above components, the first medium also contains a hormone. As used herein, hormone is intended to mean any natural or synthetic compound which has a regulatory affect on plants or plant tissue. Plant hormones include auxins and cytokinins. It has been found that the hormone which is useful for callus induction in the present invention is dicamba or chloramben. The amount of hormone present is sufficient to ensure callus formation. Generally, 5-15 $\mu$M, preferably 10 $\mu$M, is sufficient. It is preferred to use 10 $\mu$M chloramben as the hormone in the first medium. The medium is sterilized by autoclaving all of the components except the vitamins and dicamba or chloramben. The latter are sterilized by microporous membrane filtration prior to addition to the autoclaved medium.

The immature embryos are plated on the first medium and cultured in diffused light with a photoperiod of 16 hours per day for 2-4 weeks, preferably 2-3 weeks. During this time, the embryo undergoes de-differentiation and callus formation. After culturing the immature embryo on the first medium, the callus is transferred and subcultured on a maintenance medium, hereinafter referred to as the second medium. The callus is subcultured on the second medium in diffused light for 4-8 weeks. The callus can be maintained on the second medium for a longer period of time if desired. After 2-4 weeks, the callus is transferred to a fresh second medium. Any roots which have formed are removed at each transfer of the callus.

The second medium comprises mineral salts, vitamins, sucrose and a hormone in an amount sufficient to maintain the callus. The mineral salts and vitamins are as described for the first medium. As in the first medium, various combinations of mineral salts which do not adversely affect the functioning of the medium may be utilized. The sucrose concentration is 3-6%, preferably 3%. The hormone is dicamba, or preferably, chloramben and is used in the amount of 5-10 $\mu$M, with 5 uM preferred. Gelrite TM is added to the medium to solidify it. A concentration of 0.18% is satisfactory. The medium has a pH of 5.5-6.0 with 5.8 preferred. The medium is sterilized as described above.

The sucrose concentration for maintenance can be dropped to the desired level immediately or in a stepwise manner. For example, callus from first medium containing 9% sucrose can be transferred to second medium containing 3% sucrose. Alternatively, it can first be transferred to second medium containing 6% sucrose and cultured for 2-4 weeks and then transferred to second medium having 3% sucrose.

It may also be desirable to add abscisic acid (ABA) to the second medium to slow down the growth of the tissue. This is preferred for long term maintenance of the callus. When ABA is utilized, 0.1-2.0 μM, preferably 0.1-1.0 μM is used.

After culturing the callus on the second medium, it is transferred and subcultured on a regeneration medium, hereinafter referred to as the third medium and cultured in diffused light. The third medium contains the same mineral salts and vitamins as the first medium. As in the first medium, various combinations of mineral salts which do not adversely affect the functioning of the medium may be utilized. In addition, this medium contains a hormone to ensure shoot formation. It has been found that either dicamba, chloramben or a mixture of either dicamba or chloramben and 2,4-D is useful for shoot and root formation. The 2,4-D may be added to promote root formation. Generally, 0-5 μM, preferably 1 μM of dicamba or chloramben along or in combinations with 0.0.1 μM 2,4-D is utilized. It is preferred to use chloramben if any hormone is present.

It is preferred that the third medium contains 3-6% sucrose, preferably 3%, and the same amount of gelling substance as the first medium and has the same pH. This medium is also sterilized by autoclaving and membrane filtration as previously described.

In order to enhance the efficiency of plant regeneration on the third medium, it may be desirable to first transfer the maintained callus to fresh second medium having a higher sucrose concentration for 1-2 weeks before transferring it to the third medium. For example, if the callus is being maintained on second medium having 3% sucrose, the callus could first be transferred to fresh second medium having 6% sucrose before being transferred to the third medium.

Once shoots and roots have formed, they can be transferred to soil or they can optionally be transferred to a maturation medium, hereinafter referred to as the fourth medium and cultured in diffused light. The fourth medium is identical to the third medium except that it contains 1-3%, preferably 2% sucrose. It is preferred that no hormone be utilized in this medium. If one is present, then 0-1.0 μM dicamba or chloramben with or without 0-0.1 μM 2,4-D may be used.

After roots have formed, the plantlets are ready to be transferred to soil. Shoots having well established roots are removed from the tubes and the Gelrite ™ washed off. The plants are transplanted to soil having two parts potting soil and one part vermiculite and kept moist in a high humidity chamber. The plants are then transplanted to larger pots.

This process is useful for regenerating plantlets from tissue of many cultivars of corn. It is especially useful for regenerating plantlets from cultivars for which prior art methods have been unsuccessful to regenerate plants. Examples of these cultivars include B73, A632, CM105, B37, B84, B14, Mo17, R168. In addition to these cultivars, the present process is also useful to regenerate cultivars which have previously been regenerated by prior techniques. Examples of these cultivars include MS71, A188, PA91, A641, W117.

The primary difficulty with prior art systems for regenerating various cultivars of corn has been the inability to induce callus formation. In general, if a callus could be induced from corn tissue, the callus could then be processed to regenerate plants. Thus, the ability to induce callus formation is the step which limits the regeneration of several cultivars of corn. The present invention discloses a method for inducing callus formation and plant regeneration. The method of regenerating plants is applicable to all cultivars of corn once callus tissue has been formed. Consequently, in the examples which follow, the general procedure has been shown for one cultivar of corn (B73). For the remaining cultivars, only callus induction is described. The callus for each cultivar had the same general appearance as did the callus from B73. Consequently, plants can be obtained from each of these cultivars by following the procedure described herein.

The present invention will be further described by reference to the following non-limiting examples. In these examples, culturing in the light refers to culturing in diffused light having a photoperiod of 16 hours per day at 25° C. unless indicated otherwise. The temperature during the 8 hours dark phase is 25° C. unless indicated otherwise.

EXAMPLE 1

Preparation of Solutions

The following stock solutions or solutions were prepared for use in making the media described in further detail below.

1. Mineral Salts

A. Monopotassium phosphate

A 200x stock solution was prepared by dissolving 8 gm of monopotassium phosphate in 100 ml of distilled deionized water. The stock solution was stored in the refrigerator.

B. Remaining mineral salts

A 10x stock solution was prepared by dissolving 7.40 g magnesium sulfate heptahydrate, 6.64 g calcium chloride dihydrate, 113.2 g potassium nitrate, 18.52 g ammonium sulfate, 64 mg boric acid, 132 mg manganese sulfate monohydrate, 60 mg zinc sulfate heptahydrate, 33.2 mg. potassium iodide, 10 mg sodium molybdate (VI) dihydrate, 1.0 mg cooper (II) sulfate pentahydrate and 1.0 mg cobalt chloride hexahydrate in 3600 ml of distilled, deionized water. 1.112 g of iron (II) sulfate heptahydrate and 1.492 g of disodium-EDTA were individually dissolved in 200 ml of distilled, deionized water by heating and were then mixed together slowly with stirring. This mixture was then added to the remainder of the salts. The salts stock solution was divided into 100 ml aliquots and frozen until used.

2. Vitamins

A 100x stock solution of vitamins was prepared by dissolving 10 g myo-inositol, 50 mg of nicotinic acid, 200 mg glycine, 50 mg pyridoxine hydrochloride, 100 mg thiamine hydrochloride and 25 mg calcium pantothenate in 100 ml of distilled, deionized water, which was then diluted ten fold with distilled, deionized water to prepare the stock solution. 100 ml aliquots were frozen in dark bottles until used.

3. Hormones

A. Dicamba A.

A 1 mg/ml stock solution was prepared by diluting 0.21 ml of dicamba obtained from Velsicol Chemicals to 100 ml with distilled deionized water. This solution was stored in the refrigerator.

B. 2,4-D

A 0.5 mM stock solution was prepared by dissolving 11.05 mg of 2,4-D in 0.5-1.0 ml of 1.0 N KOH and diluting to 100 ml with distilled, deionized water. The pH was adjusted to 5.8 with 1.0 N HCl, and the solution was stored in the refrigerator.

C. Chloramben

A 0.55 mM stock solution was prepared as described for 2,4-D using 10.30 mg of chloramben.

D. Dicamba B.

A 0.55 mM stock solution was prepared as described for 2,4-D using 11.05 mg of dicamba.

EXAMPLE 2

Preparation of Media

1. First Medium or Callus Induction Medium

The first medium was prepared by adding 40 g of sucrose and 100 ml of the 10x mineral stock solution to 800 ml of distilled, deionized water. 5 ml of the 200x monopotassium phosphate stock solution was then added and the volume brought to one liter with distilled, deionized water. The pH was adjusted to 5.95 with 1.0 N KOH. The pH was adjusted high to compensate for the approximate 0.15 drop which normally occurs during autoclaving. 1.8 g of Gelrite ™ was added and the mixture autoclaved for 15 minutes at 15 psi. 10 ml of the 100x vitamin stock solution and 2 ml of the dicamba A stock solution were sterilized by filtration through a 0.2μ Gelman filter and then added to the cooling medium which was then poured into petri dishes or test tubes.

To prepare first medium having a different concentration of dicamba, the appropriate amount of the stock solution was used. For example, to prepare a first medium having 3 mg/l dicamba, 3 ml of the dicamba stock solution was used or if 10 μM is desired, then 20 ml of the dicamba B stock solution is used.

To prepare first medium having chloramben, the appropriate amount of the chloramben stock solution was used. For example, to prepare first medium having 10 μM chloramben, 20 ml of the choramben stock solution was used.

2. Second Medium or Maintenance Medium

The second medium was prepared as described above for the first medium except that 1 ml of the dicamba A stock solution was utilized. Second medium having other concentratons of dicamba were prepared as described above. Second medium having chloramben was prepared in the analogous manner as described above.

3. Third Medium or Regeneration Medium

The third medium was prepared as described above for the first medium except (a) 0.1 ml of the dicamba stock solution was used and (b) 0.2 ml of the 2,4-D stock solution was added to the media after the addition of the 200x monopotassium phosphate stock solution. To prepare third medium having different concentrations of hormones or containing only dicamba or chloramben or a mixture of dicamba and chloramben, the appropriate amounts of the stock solutions were added as previously described.

4. Fourth Medium or Maturation Medium

The fourth medium was prepared as described above for the first medium except (a) 20 g of sucrose and (b) 0.1 ml of the dicamba stock solution were used. Fourth medium having a different concentration of dicamba or having chloramben was prepared as described above. Fourth medium having dicamba or chloramben in combination with 2,4-D was prepared in the analogous manner as for the third medium.

EXAMPLE 3

Corn Regeneration

Immature embryos were isolated from the cob of the corn *Zea mays* L. B73 10-11 days post-pollination when they were 1.5 mm in length. The cob was harvested and surface sterilized in a solution containing 30% Clorox ® R bleach (1.6% sodium hypochlorite) and 1-2 drops/200 ml of Liquinox ® detergent for 15 minutes. The cobs were rinsed with sterile, deionized water four times. The immature embryos were isolated by slicing off the top of each kernel with a scalpel and scooping out the endosperm. The immature embryos are then taken out and plated onto the first medium, contained in a petri dish, so that the embryo axis was in contact with the medium, i.e. the scutellar side was up. The first medium was prepared as described in the preceding example using 2 mg/l dicamba. The petri dish was placed in the light and cultured for 4 weeks.

At this time, each callus was transferred to the second medium, which was prepared as described above, using 1 mg/l dicamba, and also contained in a petri dish. The callus was cultured on this medium for 6 weeks in the light with transfer to fresh medium after three weeks. At each transfer, any roots which had formed were removed from each callus.

Each callus was then transferred to the third medium. The third medium was prepared as described in Example 2, using 0.1 mg/l dicamba and 0.1 μM 2,4-D. The callus was cultured on this medium in the light for 5 days. The callus differentiated to form shoots and roots.

The shoots with roots were then transferred to the fourth medium, contained in culture tubes. The fourth medium was prepared as described above, using 0.1 mg/l dicamba. The shoots with roots were cultured in the light for 1-2 weeks during which additional roots formed.

The plantlets were transferred to soil in the greenhouse. Shoots with well established roots were removed from the tubes and the Gelrite ™ was thoroughly washed off with tap water. The plantlets were placed in potting cubes containing two parts potting soil and one part vermiculite. The potting cubes were placed in a high humidity chamber and kept moist for five days. The lid of the chamber was then removed. After three more days the plants were transplanted to 12" pots. The plants were watered 2-3 times per week and fertilized every two weeks.

EXAMPLE 4

Callus Induction

Immature embryos were isolated from the following cultivars of corn and plated onto first medium as described in Example 3: *Zea mays* L. A632, A619, CM105, B37, B84, B14, M017, R168, MS71, A641 and W117 except sucrose concentration was either 3% or 9%. Callus was obtained and had the same or better general appearance as the callus of Example 3 for each cultivar. Each callus was ready for transfer to the second medium.

EXAMPLE 5

Callus Induction

Immature embryos were isolated from *Zea mays* L. B73 and MS71 as described in Example 3. The embryos were plated onto first medium containing 10 μM chloramben and either (a) 3%, (b) 6%, (c) 9% or (d) 12% sucrose. Callus was obtained and had the same general appearance as the callus of Example 3 in each instance except for B73 on 3% sucrose. First medium having 9% or 12% sucrose was found to be better for callus induction. Each callus was ready for transfer to the second medium.

EXAMPLE 6

Callus Induction

Immature embryos were isolated as described in Example 3 from the corn cultivars identified in Examples 3 and 4. The embryos were plated onto first medium containing 10 μM chloramben and either 9% or 3% sucrose. Callus was obtained and had the same general appearance as the callus of Example 3 for each cultivar except B73 on 3% sucrose. Each callus was ready for transfer to second medium.

While the invention has been described in connection with specific embodiments thereof, it will be understood that it is capable of further modifications. This application is intended to cover any variations, uses or adaptations of the invention following, in general, the principles of the invention and including such departures from the present disclosure as come within known and customary practice within the art to which the invention pertains.

What is claimed is:

1. A process for regenerating corn plantlets from cell or tissue culture which comprises the steps of:
   (a) culturing tissue obtained from a corn plant on a first medium comprising mineral salts, vitamins, sucrose and a hormone selected from the group consisting of chloramben and dicamba for callus formation;
   (b) subculturing said callus on a second medium comprising mineral salts, vitamins, sucrose and a hormone selected from the group consisting of chloramben, dicamba, a mixture of chloramben and ABA, and a mixture of dicamba and ABA for callus maintenance; and
   (c) subculturing said callus on a third medium comprising mineral salts, vitamins and sucrose for shoot and root formation, whereby plants are obtained.

2. The process of claim 1 wherein said tissue is obtained from immature embryo.

3. The process of claim 1 wherein said shoots and roots are subcultured on a fourth medium comprising mineral salts, vitamins and sucrose.

4. The process of claim 1 wherein said third medium further comprises a hormone selected from the group consisting of chloramben, dicamba, a mixture of chloramben and 2,4-D, and a mixture of dicamba and 2,4-D.

5. The process of claim 3 wherein said fourth medium further comprises a hormone selected from the group consisting of chloramben, dicamba, a mixture of chloramben and 2,4-D, and a mixture of dicamba and 2,4-D.

6. The process of claim 4 wherein said shoots and roots are subcultured on a fourth medium comprising mineral salts, vitamins and sucrose.

7. The process of claim 6 wherein said fourth medium further comprises a hormone selected from the group consisting of chloramben, dicamba, a mixture of chloramben and 2,4-D, and a mixture of dicamba and 2,4-D.

8. The process of claim 1 wherein the concentrations of said hormones are:
   (1) 5–15 μM chloramben or 5–15 μM dicamba in said first medium; and
   (2) 5–10 μM chloramben, 5–10 μM dicamba, 5–10 μM chloramben and 0.1–2 μM ABA or 5–10 μM dicamba and 0.1–2 μM ABA in said second medium.

9. The process of claim 3 wherein the concentrations of said hormones are:
   (1) 5–15 μM chloramben or 5–15 μM dicamba in said first medium; and
   (2) 5–10 μM chloramben, 5–10 μM dicamba, 5–10 μM chloramben and 0.1–2 μM ABA or 5–10 μM dicamba and 0.1–2 μM ABA in said second medium.

10. The process of claim 4 wherein the concentrations of said hormones are:
    (1) 5–15 μM chloramben or 5–15 μM dicamba in said first medium; and
    (2) 5–10 μM chloramben, 5–10 μM dicamba, 5–10 μM chloramben and 0.1–2 μM ABA or 5–10 μM dicamba and 0.1–2 μM ABA in said second medium, and
    (3) about 0.1–5 μM chloramben, about 0.1–5 μM dicamba, about 0.1–5 μM chloramben and about 0.1 μM 2,4-D or about 0.1–5 μM dicamba and about 0.1 μM 2,4-D in said third medium.

11. The process of claim 5 wherein the concentrations of said hormones are:
    (1) 5–15 μM chloramben or 5–15 μM dicamba in said first medium; and
    (2) 5–10 μM chloramben, 5–10 μM dicamba, 5–10 μM chloramben and 0.1–2 μM ABA or 5–10 μM dicamba and 0.1–2 μM ABA in said second medium, and
    (3) about 0.1–1 μM chloramben, about 0.1–1 μM dicamba, about 0.1–1 μM chloramben and about 0.1 μM 2,4-D or about 0.1–1 μM dicamba and about 0.1 μM 2,4-D in said fourth medium.

12. The process of claim 6 wherein the concentrations of said hormones are:
    (1) 5–15 μM chloramben or 5–15 μM dicamba in said first medium; and
    (2) 5–10 μM chloramben, 5–10 μM dicamba, 5–10 μM chloramben and 0.1–2 μM ABA or 5–10 μM dicamba and 0.1–2 μM ABA in said second medium, and
    (3) about 0.1–5 μM chloramben, about 0.1–5 μM dicamba, about 0.1–5 μM chloramben and about 0.1 μM 2,4-D or about 0.1–5 μM dicamba and about 0.1 μM 2,4-D in said third medium,.

13. The process of claim 7 wherein the concentrations of said hormones are:
    (1) 5–15 μM chloramben or 5–15 μM dicamba in said first medium; and
    (2) 5–10 μM chloramben, 5–10 μM dicamba, 5–10 μM chloramben and 0.1–2 μM ABA or 5–10 μM dicamba and 0.1–2 μM ABA in said second medium, and
    (3) about 0.1–5 μM chloramben, about 0.1–5 μM dicamba, about 0.1–5 μM chloramben and about 0.1 μM 2,4-D or about 0.1–5 μM dicamba and about 0.1 μM 2,4-D in said third medium, and
    (4) about 0.1–1 μM chloramben, about 0.1–1 μM dicamba, about 0.1–1 μM chloramben and about 0.1 μM 2,4-D or about 0.1–1 μM dicamba and about 0.1 μM 2,4-D in said fourth medium.

14. The process of claim 8 wherein the concentration of sucrose is
    (1) 3–12% in said first medium; and
    (2) 3–6% in said second and third media.

15. The process of claim 9 wherein the concentration of sucrose is (1) 3–12% in said first medium;
(2) 3–6% in said second and third media; and
(3) 1–3% in said fourth media.

16. The process of claim 10 wherein the concentration of sucrose is
(1) 3–12% in said first medium; and
(2) 3–6% in said second and third media.

17. The process of claim 11 wherein the concentration of sucrose is
(1) 3–12% in said first medium;
(2) 3–6% in said second and third media; and
(3) 1–3% in said fourth media.

18. The process of claim 12 wherein the concentration of sucrose is
(1) 3–12% in said first medium;
(2) 3–6% in said second and third media; and
(3) 1–3% in said fourth media.

19. The process of claim 13 wherein the concentration of sucrose is
(1) 3–12% in said first medium;
(2) 3–6% in said second and third media; and
(3) 1–3% in said fourth media.

* * * * *